United States Patent
Cade et al.

(10) Patent No.: US 10,525,011 B2
(45) Date of Patent: Jan. 7, 2020

(54) DOSAGE FORM ARTICLES FOR EXTERNAL MUCOSAL APPLICATIONS

(71) Applicant: Capsugel Belgium NV, Bornem (BE)

(72) Inventors: Dominique Nicolas Cade, Colmar (FR); Hugues Straub, Colmar (FR)

(73) Assignee: Capsugel Belgium NV, Bornem (BE)

( * ) Notice: Subject to any disclaimer, the term of this patent is extended or adjusted under 35 U.S.C. 154(b) by 240 days.

(21) Appl. No.: 15/523,661

(22) PCT Filed: Nov. 16, 2015

(86) PCT No.: PCT/EP2015/076641
§ 371 (c)(1),
(2) Date: May 1, 2017

(87) PCT Pub. No.: WO2016/083168
PCT Pub. Date: Jun. 2, 2016

(65) Prior Publication Data
US 2017/0312228 A1 Nov. 2, 2017

(30) Foreign Application Priority Data
Nov. 27, 2014 (EP) .................................. 14195290

(51) Int. Cl.
*A61K 9/48* (2006.01)
*A61K 47/38* (2006.01)
*A61K 47/36* (2006.01)
*A61K 9/00* (2006.01)

(52) U.S. Cl.
CPC .......... *A61K 9/4891* (2013.01); *A61K 9/0034* (2013.01); *A61K 9/4808* (2013.01);
(Continued)

(58) Field of Classification Search
CPC ...... A61K 9/4891; A61K 47/38; A61K 47/36; A61K 9/0034; A61K 9/4808; A61K 9/4883; A61K 9/4816
See application file for complete search history.

(56) References Cited

U.S. PATENT DOCUMENTS

| | | | |
|---|---|---|---|
| 4,816,259 A | 3/1989 | Matthews et al. | |
| 8,105,625 B2 | 1/2012 | Rajewski et al. | |
| 2008/0248102 A1* | 10/2008 | Rajewski | A61K 9/0056 424/452 |

(Continued)

FOREIGN PATENT DOCUMENTS

| | | |
|---|---|---|
| CA | 2965425 | 6/2016 |
| EP | 0210325 | 2/1987 |

(Continued)

OTHER PUBLICATIONS

International Preliminary Report on Patentability for PCT/EP2015/076641 (dated Jun. 8, 2017).
(Continued)

*Primary Examiner* — Trevor Love
(74) *Attorney, Agent, or Firm* — Klarquist Sparkman, LLP (57) ABSTRACT

A dosage form article consisting of a hard capsule coated with a surface modifying coating wherein the coating is an aqueous composition comprising water and a muco-adhesive polymer selected from the group consisting of poly (acrylates), cellulose derivatives, hyaluronic acid, starch, poly(ethylene glycol), polysaccharides, collagen derivatives, and mixtures thereof, wherein the ratio of the muco-adhesive polymer to water is less than 0.15 by weight of the coating composition.

18 Claims, 2 Drawing Sheets

(52) U.S. Cl.
CPC .......... *A61K 9/4816* (2013.01); *A61K 9/4883* (2013.01); *A61K 47/36* (2013.01); *A61K 47/38* (2013.01)

(56) References Cited

U.S. PATENT DOCUMENTS

2013/0005831 A1    1/2013   Rajewski et al.

FOREIGN PATENT DOCUMENTS

| EP | 2596797 | 5/2013 | | |
|---|---|---|---|---|
| EP | 3025709 | 6/2016 | | |
| FR | 2118883 | 8/1972 | | |
| JP | 2003306428 | 10/2003 | | |
| JP | 2010523594 | 7/2010 | | |
| JP | 2018500278 | 1/2018 | | |
| WO | WO2005/101983 | 11/2005 | | |
| WO | WO2013150331 | 10/2013 | | |
| WO | WO2013150331 | * 10/2013 | ............... | A61K 9/48 |
| WO | WO2013/174884 | 11/2013 | | |
| WO | WO2013/181449 | 12/2013 | | |
| WO | WO2016083168 | 6/2016 | | |

OTHER PUBLICATIONS

Office Action from European Patent Office for European Application No. 14195290.3 (dated Mar. 22, 2018).

"ACRYL-EZE Application Data Aqueous Acrylic Enteric System Aqueous Enteric Coating Application on Non-Banded Hard Gelatin," Jan. 1, 2002 (Jan. 1, 2002), XP055184775, Retrieved from the Internet <URL:http://www.colorcon.com/literature/marketing/mr/Delayed Release/Acryl-EZE/English/ads_acryleze_aqu_ent_coat.pdf> [retrieved on Apr. 21, 2015].

Cade et al., "Liquid Filling in Hard Gelatin Capsules—Preliminary Steps," Bulletin Technique Gattefosse (1996).

das Neves et al., "Performance of an in vitro mucoadhesion testing method for vaginal semisolids: Influence of different testing conditions and instrumental parameters," *European Journal of Pharmaceutics and Biopharmaceutics*, 69(2):622-632 (Jun. 2008).

International Search Report and Written Opinion for PCT/EP2015/076641, dated Jan. 7, 2016.

Owen et al., "A vaginal fluid simulant," *Contraception*, 59(2):91-95 (Feb. 1999).

Thoma et al., "Enteric coated hard gelatin capsules," Jan. 1, 2000 (Jan. 1, 2000), XP055184774, Retrieved from the Internet <URL:http://capsugel.com/media/library/enteric-coated-hard-gelatin-capsules.pdf> [retrieved on Apr. 21, 2015].

Office Action from European Patent Office for European Application No. 14195290.3 (dated Mar. 26, 2019).

Office Action from Japanese Patent Office for Japanese Application No. 2017-521503 (dated May 20, 2019 (with machine translation).

Ohta et al., "Preparation and Dissolution Characteristics of Pullulan Tablets," *Kobunshi Ronbunsyu*, 42(11):809-816 (Nov. 1985) (English abstract).

* cited by examiner

DOSAGE FORM ARTICLES FOR EXTERNAL MUCOSAL APPLICATIONS

CROSS REFERENCE TO RELATED APPLICATIONS

This is the U.S. National Stage of International Application No. PCT/EP2015/076641, filed Nov. 16, 2015, which in turn claims the benefit of and priority to European Patent Application No. 14195290.3, filed Nov. 27, 2014.

FIELD

The present disclosure relates to dosage form articles for the delivery of one or more drugs/medicaments (or health and nutrition materials) via oral, vaginal, rectal or other, administration of the same to a subject. More particularly, the dosage form articles are comestible and suitable for assimilation by a subject, preferably the subject being selected from humans or animals.

BACKGROUND

Receptacle technology, and in particular capsule technology, continues to be subject to development and improvements and so does the manufacture thereof, including processes and equipment. In its basic form, standard containers for pharmaceuticals or other powdered, granular or liquid substances (generally referred to as telescope-type or two-piece capsules) include a tubular-shaped and/or cylindrically-shaped first part, namely a cap part, which is closed on one end and open on the other opposite end. A tightly fitting second part of similar shape, namely the body part, is of smaller diameter than the cap part and is typically telescopically engaged therein to form the overall dosage form or two-piece capsule. Similar capsule technology may be used to generate multi-compartment capsules.

Such dosage form articles have been implemented for delivery of active ingredients to humans and animals via several different forms of administration such as oral, vaginal, and rectal. Vaginal drug delivery for both local action and systemic effects offers advantages compared to other routes because of its large surface area and dense network of blood vessels that favors absorption. It also avoids the hepatic first-pass effect and gastro-intestinal route. As a discreet self-inserted form, it presents good permeability to a variety of drugs as well.

Examples of dosage forms that have been implemented particularly in vaginal applications are described in EP 2 596 797 A1 and WO2013/181449 A1. The former describes a capsule made of a polysaccharide for vaginal use and the latter describes a pullulan comprising capsule also for vaginal use.

Although different drug delivery systems for vaginal applications are available on the market, a need still exists to further develop dosage form articles that more effectively meet the clinical and patient requirements being: 1) a dosage form having prolonged residence time, 2) of which content is quickly released to obtain fast absorption and/or to maximize the treatment action in contact with the vaginal mucosa, and/or 3) that is easy to put in place without causing discomfort over time because of possible leakages or losses.

SUMMARY

A first aspect of the present disclosure relates to a dosage form article consisting of a hard capsule coated with a surface modifying coating wherein the coating is an aqueous composition comprising water and a muco-adhesive polymer selected from the group consisting of poly(acrylates), cellulose derivatives, hyaluronic acid, starch, poly(ethylene glycol), polysaccharides, collagen derivatives, and mixtures thereof, wherein the ratio of the muco-adhesive polymer to water is less than 0.15 by weight of the coating composition.

A further aspect of the present disclosure relates to a method for transmucosal administration of an active agent, preferably a medicament, comprising the step of administering a dosage form article described herein to the external mucosa of a subject, typically vaginal mucosa of a female subject.

A further aspect of the present disclosure relates to the use of an aqueous coating as described herein for imparting adhesiveness and rapid capsule disintegration to a hard capsule coated therewith, preferably when contacted with a mucosal tissue of a subject.

DETAILED DESCRIPTION

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which substantially returns to its un-deformed shape upon the removal of a deforming force. Typically such shells comprise less than 25%, preferably less than 20%, more preferably from 0% to 14%, even more preferably from greater than 0% to less than 14%, water by weight.

By the term "rapid capsule disintegration", it is intended that full disintegration of the coated capsule (according to the USP disintegration <701> method described in the full disintegration method reported herein) is achieved at a time that is at least 20%, preferably at least 25%, more preferably at least 30%, less than the time taken by the capsule free of coating.

By the term "adhesiveness", it is intended the adhesive properties provided to the element referred to, according to the test methods described herein.

By the terms "taste modifying" or "taste masking", it is intended components that are intended to encompass agents (i.e., chemical substances) that mask tastes, such as a bitter or unpleasant tastes/flavors, or agents (i.e., chemical substances) which modify taste, such as an ingredient added to the formulation or composition and which renders a bitter or unpalatable taste or flavor more palatable. The modification of taste by the taste modifying or taste masking ingredient is typically one in which an unpleasant taste is significantly reduced and usually rendered sweeter and/or more palatable. The embodiments disclosed herein are intended for consumption by humans or other mammals.

By the term "oral administration" as used herein, it is intended that the dosage form referred to is to be placed in the buccal cavity of the subject and is retained therein at least until its contents is released in said buccal cavity, preferably wherein the dosage form is dissolved, typically fully disintegrated, in said buccal cavity. A distinction is therefore made with dosage forms for ingestion (and/or swallowing) via the oral route wherein the contents is not to be released in the buccal cavity.

By the terms "mucosa" or "mucosal tissue" as used herein, it is intended external mucosa, typically excluding internal mucosa, said external mucosa typically including vaginal mucosa, buccal mucosa and/or rectal mucosa, preferably vaginal mucosa.

By the term "internal mucosa" it is intended mucosa in regions that are not proximal to an external part of the subject's body, these include esophageal mucosa, gastric mucosa, intestinal mucosa and the like.

Various embodiments will now be described to provide an overall understanding of the principles of the structure, function, manufacture, and use of dosage forms, uses, and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

The Dosage Form Article

In its basic form, the dosage form articles herein are in the form of coated hard capsules for delivery of an active material (or medicament) to a subject.

The hard capsules herein are typically suitable for vaginal administration (or oral administration or rectal administration, preferably vaginal administration) and comprise a surface modifying coating wherein said coating is an aqueous composition comprising water and a muco-adhesive polymer selected from the group consisting of polyacrylates, cellulose derivatives, hyaluronic acid, starch, polyethylene glycol, polysaccharides, collagen derivatives, and mixtures thereof, wherein the ratio of said muco-adhesive polymer to water is less than 0.15 by weight of said coating. Typically, said ratio is determined for the liquid coating composition being applied to the capsule. The hard capsule herein may have a polymer/water weight ratio that is from greater than 0 to 0.12, preferably from 0.010 to 0.1, more preferably from 0.010 to 0.050, more preferably from 0.010 to 0.025, even more preferably from 0.010 to 0.020, even more preferably from 0.010 to 0.018, most preferably from 0.010 to 0.015. Without wishing to be bound by theory, it is believed that higher ratios of polymer would result in a substantial increase in brittleness of the capsule with negligible further adhesive benefits, as well as a drop in dissolution benefits.

Suitable polyacrylates for use in coatings herein include polymer comprising acrylic acid selected from the group consisting of copolymers of acrylic acid, polycarbophul, crosslinked homopolymers of acrylic acid, polyacrylic homopolymers, carbomers, Carbopol 974P-NF, Carbopol 971P-NF, EDT resin, copolymers of acrylic acid and C10 to C30 alkyl acrylic acid, and mixtures thereof.

Suitable cellulose derivatives for use in coatings herein include methylcellulose, alkylcellulose, hydroxypropyl cellulose, hydrohyalkyl cellulose, hydroxypropylmethyl cellulose or hypromellose, carboxymethyl cellulose, hydroxypropylmethyl cellulose acetate succinate, hydroxypropylmethyl cellulose phthalate, cellulose acetate phthalate, sodium carboxymethylcellulose, and mixtures thereof, preferably hypromellose.

Suitable starches for use in coatings herein include corn starch, potato starch, tapioca starch, rice starch, pea starch, modified starch or pregelatinized starch, high-amylose starch, substituted starch such as hydroxypropyl starch or starch succinate or starch acetate, crosslinked starch such as starch phosphate, hydrolyzed starch, carboxymethyl starch, sodium starch glycolate, amylose, and mixtures thereof.

Suitable polyethylene glycols for use in coatings herein include polyethylene glycol of molecular weight up to 6000, more preferably up to 4000.

Suitable polysaccharides for use in coatings herein include pullulan, carrageenan, anionic polysaccharides like Na-alginate, natural gums like tragacanth, Karaya, or Arabic gum, heteropolysaccharides like pectin, or gellan gum, or acacia gum, linear polysaccharides like cationic chitosan, galactomannan, and mixtures thereof, preferably pullulan.

Suitable collagen derivatives for use in coatings herein include gelatin from bovine, porcine or fish source.

It has surprisingly been found that capsules coated with the coating described herein not only provide exceptional adhesion to mucosal tissue but further increases the speed at which the capsule disintegrates, hence providing both secure location of the capsule onto a mucosal surface (i.e. remain in place and not dislodge under gravity or other forces caused by movement of the subject) and immediate (or fast release) of the substances contained therein.

The coating may be present in an amount of less than 2.5%, preferably less than or equal to 2%, more preferably from 0.2% to 1.8%, even more preferably from 0.5% to 1.5%, most preferably from 0.5% to 1%, by weight of the empty capsule. Coatings above these ranges would provide negligible adhesion benefits and rather increase the brittleness of the capsules as well as added cost.

The muco-adhesive polymer may comprise, preferably consist of, a Carbomer and/or poly(acrylate) selected from one or more carboxypolymethylenes, preferably having an average particle size of less than 0.5 microns, preferably from 0.1 to 0.3 microns. Typically, said carboxypolymethylene may comprise a homopolymer of acrylic acid polymerized in ethyl acetate and crosslinked with a polyalkenyl polyether. An example of suitable commercially available carboxymethylene is Carbopol (from Lubrizol), preferably Carbopol 974P NF (from Lubrizol) or Carbopol 971P NF (from Lubrizol).

In an embodiment, the coating comprises at least two muco-adhesive polymers wherein at least one is selected from poly(acrylates), and at least one other is selected from the group consisting of hyaluronic acid, starch, poly(ethylene glycol), polysaccharides, collagen derivatives, and mixtures thereof. In a preferred embodiment, the at least two muco-adhesive polymers comprise a carboxypolymethylenes, preferably having an average particle size of less than 0.5 microns, preferably from 0.1 to 0.3 microns, and a polysaccharide, preferably pullulan.

In an embodiment the muco-adhesive polymer is present in an amount of from 0.5% to 15%, preferably from 0.5% to 10%, more preferably from 0.5% to 5%, more preferably from 0.5% to 3%, even more preferably from 0.5% to 2%, most preferably from 0.5% to 1.5%, by weight of the coating composition.

In an embodiment, the coating may further comprise one or more plasticizers, preferably selected from the group consisting of non-ionic glyceryl esters (e.g. glyceryl monooleate and monolinoleate, medium chain triglycerides—i.e. C6-C12 fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); or polyoxyethylene-polyoxypropylene-polyoxyethylene tri-block copolymers (e.g. poloxamer);

or phtalique esters (e.g. dimethyl-, diethyl-, dibutyl-, diisopropyl- and dioctyl-phtalate); citric esters (e.g. triethyl-, tributyl-, acetyltriethyl- and acetyltributyl-citrate); phosphoric esters (e.g. triethyl-, tricresyl, triphenyl-phosphate); alkyl lactate; glycerol and glycerol esters (e.g. glycerol triacetate also known as triacetine); sucrose esters; oils and fatty acid esters; butyl stearate; dibutyl sebacate; dibutyl tartrate; diisobutyl adipate, tributyrin; propylene glycol; polyethyleneglycol (PEG), polyoxyethylene (PEO); sodium lauryl sulfate, or mixtures of thereof.

In an embodiment, the plasticizer is present at a level of from 0.1% to 5%, preferably from 0.1% to 3%, more preferably from 0.1% to 2%, even more preferably from 0.1% to 1%, most preferably from 0.1% to 0.5%, by weight of said coating composition. Such may reduce the brittleness of the capsule and allow higher levels of muco-adhesive polymers to be used.

The coating may further comprise one or more taste masking components. A non-limiting taste modifying component or agent contemplated in certain embodiments is steviol glycoside, a naturally extracted sweetener from the *Stevia* plant native to South America. The steviol glycosides are responsible for the sweet taste of the leaves of the *stevia* plant (*Stevia rebaudiana* Bertoni). These compounds range in sweetness from 40 to 300 times sweeter than sucrose. They are heat-stable, pH-stable, and do not ferment. Suitable examples are described in WO2013/174884. They also do not induce a glycemic response when ingested, making them attractive as natural caloric-free sweeteners to diabetics and others on carbohydratecontrolled diets. The sweet substance extracted from the *stevia* plant is based on steviol and glucose units forming the steviol glycoside family; there are 9 different chemical structures among which the two main compounds, stevioside and rebaudioside A, have respectively 2 and 3 linked glucose molecules to the steviol chemical structure. The seven other steviol glycosides are called rebaudioside B, C, D, E, Dulcoside A, B and steviolbioside. Stevioside, rebaudioside A and their blends are the main sweet natural products available commercially. The richer the blend in rebaudioside A, the sweeter and least bitter the taste. High levels of stevioside also tend to leave a licorice aftertaste. Depending on the degree of rebaudioside purity, various grades of commercial steviol glycosides (also known as *stevia* extracts) are available under the names Rebaten or Steviten from SEPPIC or DAEPYUNG Company. Without wishing to be bound by theory, the presence of such further components further improves consumer/subject acceptance of the capsule and provides an added perception of fast dissolution.

In a preferred embodiment, the coating consists of: water, the muco-adhesive polymer(s), one or more plasticizers and optionally one or more dissolution enhancers preferably selected from the group consisting of glycerol, mannitol, polydextrose, maltose, polysorbate, sorbitol, xylitol, dextrose, propylene glycol, polyethylene glycol, poloxamer, starch and modified starch, guar gum, pectin, locust bean and xanthan gums, sodium alginate, carboxymethylcellulose, crospovidone, croscarmellose, polyvinylpyrrolidone, pullulan, hypromellose, citric acid, tartaric acid, lactic acid, fumaric acid, malic acid, ascorbic acid, succinic acid, and mixtures thereof.

Dissolution enhancers may also include sugars such as mannitol, sorbitol, xylitol, glucitol, ducitol, inositol, arabinitol, arabitol, galactitol, iditol, allitol, fructose, sorbose, glucose, xylose, trehalose, dextrose, galactose, talose, ribose, arabinose, sucrose, maltose, lactose, fucose, matotriose, and the like, and mixtures thereof. Suitable dissolution enhancers include taste masking and/or taste modifying components as described herein above.

In an embodiment, the coating is applied to the capsule in the form of a liquid, typically by spraying or dipping or other suitable means. An advantage of such arrangement is to enable coating of the entire outer surface of the capsule in a homogeneous way and prevent dislodging of the coating during for example handling and/or transportation.

In a preferred embodiment, at least 80%, preferably at least 90%, more preferably 100%, of the outer surface of said capsule is coated with said coating. Indeed, it is desirable to coat the entire outer surface of the capsule in order to provide a homogenous coating therethrough.

In an embodiment, the capsule is made of a shell material comprising gelatin, hydroxypropyl methylcellulose (HPMC), pullulan, or mixtures thereof, preferably pullulan. When the capsule comprises pullulan, the pullulan may be selected from mono-, di-, and oligosaccharides free pullulan. The mono-, di-, and oligosaccharides free pullulan may have a molecular weight of from 100 KDa to 400 KDa and may have a melt viscosity, at 60° C., of from 500 to 1500 mPa·s.

The capsule shell material may further comprise a setting system. The setting system may comprise one or more materials selected from the group consisting of alginates, agar gum, guar gum, locust bean gum (carob), carrageenan, gellan gum, tara gum, gum arabic, ghatti gum, Khaya grandifolia gum, tragacanth gum, karaya gum, pectin, arabian (araban), xanthan, starch, Konjac mannan, galactomannan, funoran or exocellular polysaccharides such as acetan, welan, rhamsan, furcelleran, succinoglycan, scleroglycan, schizophyllan, tamarind gum, curdlan, pullulan and/or dextran.

Capsules herein may further comprise one or more materials selected from the group consisting of surfactants, sequestering agents, plasticizers, dyes and/or coloring agents, sweeteners, flavoring agents and/or taste masking agents. Suitable capsules for use herein include pullulan capsules marketed under the name Plantcaps® (by Capsugel).

In an embodiment, the dosage forms herein have a disintegration time of less than 100 seconds, preferably less than 95 seconds, more preferably less than 90 seconds, according to the disintegration test method described herein.

In an embodiment, the dosage forms herein have a first opening time of less than 3 minutes, preferably less than 2.8 minutes, according to the vaginal disintegration test method described herein.

In an embodiment, the dosage forms herein have a buccal disintegration time of less than 20 seconds, preferably less than 18 seconds, according to the buccal disintegration test method described herein.

Medicament

Drugs (i.e. medicaments) suitable for use in the dosage form articles described herein may take any form and be for any treatment of a human or animal subject. This includes not only pharmaceutical compounds but also dietary supplements such as vitamins, minerals and the like.

The drug may be in a state selected from solid or liquid, preferably solid, at room temperature and atmospheric pressure, and comprises one or more active compounds.

Suitable compounds (and generally encompassed by the term "medicament" as used herein) for delivery according to the disclosure include, but are not limited to, particulate, powder, waxy, liquid, and/or pellet forms of the following: a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovir-mononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydro-genmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclo-pramide, acemetacin, ranitidine, biperiden, metamizol, doxepin, dipotassiumchloraze-pat, tetrazepam, estramustinephosphate, terbutaline, captopril, maprotiline, prazosin, atenolol, glibenclamid, cefaclor, etilefrin, cimetidine, theophylline, hydromorphone, ibu-profen, primidone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitryptiline, caproteron, sodium valproinate, mebeverine, bisacodyl, 5-amino-salicyclic acid, dihydralazine, magaldrate, phenprocou-mon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), anti-emetics, anticonvulsants, antiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosphonate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylsti I bestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, oils such as krill oil and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS;

f) probiotics and yeast, such as bacteria selected from the group consisting of *Lactobacillus* (Doderlein's bacilli) such as *Lactobacillus crispatus, Lactobacillus jensinii, Lactobacillus johnsonii, Lactobacillus gasseri, Enterococcus faecium*, or fungi selected from the group of Saccharomycetales such as *Saccharomyces boulardii*.

g) hormones, such as estrogen (i.e. a natural estrogen or a synthetic compound that mimics the physiological effect of natural estrogens) including, without limitation, estradiol (17-estradiol), estridiol acetate, estradiol benzoate, estridiol cypionate, estridiol decanoate, estradiol diacetate, estradiol heptanoate, estradiol valerate, 17a-estradiol, estriol, estriol succinate, estrone, estrone acetate, estrone sulfate, estropipate (piperazine estrone sulfate), ethynylestradiol (17a-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof; or progestin (i.e. natural or synthetic compounds that possesses progestational activity including, without limitation, nortestosterone, ethynyltestosterone, deacetylnorgestimate, hydroxyprogesterone, 19-norprogesterone, 3P-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, demegestone, desogestrel, dienogest, dihydrogesterone, dimethisterone, drospirenone, dydrogesterone, ethisterone (pregneninolone, 17a-ethynyltestosterone), ethynodiol diacetate, fluorogestone acetate, gastrinone, gestadene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrol), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17a-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tanaproget, tibolone, trimegestone, or combinations thereof.
and mixtures in any combination of the foregoing.

The Methods and Uses

In an embodiment, the methods herein comprise a method for transmucosal administration of an active agent, preferably a medicament, comprising the step of administering a hard capsule as described herein above to the vaginal mucosa of a female subject. Preferably, the hard capsule is applied and subsequently released at a desired target position of the mucosa of the female subject via an applicator, typically arranged such to prevent the subject from contacting said capsule immediately prior to and/or during said positioning.

In an alternative embodiment, the methods herein comprise a method for oral administration of an active agent, preferably a medicament, comprising the step of administering a hard capsule as described herein above to the buccal cavity of a subject. Typically allowing the capsule to remain within the buccal cavity until the contents of said capsule are released and/or the capsule is completely dissolved.

In an alternative embodiment, the methods herein comprise a method for rectal administration of an active agent, preferably a medicament, comprising the step of administering a hard capsule as described herein above to the rectal cavity of a subject.

The aqueous coatings disclosed herein may be useful for imparting adhesiveness and rapid capsule disintegration of a hard capsule coated therewith, preferably when contacted with a mucosal substance (e.g. vaginal, oral or rectal, preferably vaginal).

Test Methods
Adhesion Test

Test method adapted from ADH3/P6 "Stickiness measurement of adhesive gum with the use of a cylinder probe", Texture Analyzer from Stable Micro Systems, Godalming, Surrey, U.K.

Capsule is pre-wet with 0.2 mL of simulated vaginal buffer pH 4.0 at 37° C.
Capsule is placed on the aluminum support of the texture analyzer kept at 37° C.
Upper part of texture analyzer (TA) is brought into contact with the capsule
4 kg of pressure is applied on the closed unfilled capsule
Excess of fluid is remove with an absorbing paper around the TA probe
Pressure is held on the capsule during 3 min of time
Traction force is applied onto the whole capsule by TA probe until its separation from support
The maximum force required to break the adhesive bond is measured and defined as adhesive tensile force Bio-Adhesion Test Test method adapted from ADH3/P6 "Stickiness measurement of adhesive gum with the use of a cylinder probe", Texture Analyzer from Stable Micro Systems; also described in the literature by J. das Neves et al., *European Journal of Pharmaceutics and Biopharmaceutics* 69 (2008) 622-632.

Pieces of pig vaginal mucosa (kindly supplied by the slaughterhouse of Haut-Rhin, Cernay, France) are used.

A piece (about 6×8 cm) of animal vaginal mucosa (pig) is strongly fixed on the texture analyzer flat plate maintained at constant 37° C. (use of waterproof double-sided tape and rubber bands)
A $2^{nd}$ piece of vaginal mucosa (about 7×7 cm) is also strongly fixed the same way on the upper probe of the texture analyzer (TA)
One capsule (size 1) is placed between both pig vaginal mucosa's
Capsule is pre-wet with 0.2 mL of simulated vaginal fluid at 37° C. (buffer pH 4 according to USP 4.1.3 or Owen & Katz's simulant: Owen, D. H.; Katz, D. F; A vaginal fluid stimulant. *Contraception* 1999, 59 (2), 91-95)
Upper part (probe) of TA is brought into contact with the capsule
A certain amount of pressure is applied on the closed unfilled capsule; typically 500 g pressure to better match real physiological conditions (muscles contractions and motions). Lower pressure values are considered as not discriminating enough.
Excess of fluid is remove with an absorbing paper around the TA probe
Pressure is held on the capsule during a defined period of time; typically 300 sec
Then a traction force is applied by the TA probe until separation of both parts
The maximum force required to break the adhesive bond is measured and defined as adhesive tensile force Full Disintegration Test This test enables to know the time for complete disintegration of the capsule.

Test according to USP <701> disintegration method, pp. 2670-2672.

A suitable test procedure with automated en-point is given as follows:

Sotax DT2 apparatus basket-rack assembly consisting of six open-ended transparent tubes, each tube being provided with a disk; disintegration media: demineralized water; Test conditions: fluid kept at 37° C.; oscillation frequency is 30 per minutes; volume of disintegration medium is 700 ml; number of samples tested is 6. Test shells #1 are pre-filled with 400 mg of lactose comprising 0.1% of blue dye B2. Capsules are placed in the tubes and a disk is over imposed. The basket is then placed and moved in water until full disintegration (automated end-point).

Vaginal Disintegration

This in vitro test enables to know the time required to first liberate the capsule content (first capsule opening) and the time to fully release the capsule content.

The test is described by the European Pharmacopeia 2.9.2 for suppositories and pessaries. There is little surface contact of the capsule with the simulated vaginal fluid at 37° C. (buffer pH 4 according to USP 4.1.3 or Owen & Katz's simulant) without agitation. The capsule filling content (e.g. commercial probiotic) also comprises a blue dye to better visualize the disintegration.

Buccal Disintegration

This in vivo blind test enables to know the time required to first liberate the capsule content, also indicated by the first feeling in the mouth or on the tongue of the capsule content. The capsule is filled with sugar granules, also called Sugar Granules of 0.5 mm supplied by Hanns G; Werner GmbH Germany. Five volunteers have blindly placed a capsule in their mouth and registered the time taken to have the first feel of the sweet sugar granules, under the tongue action with salivation but without mastication or chewing.

Results below 30 sec are considered as good, according to the recommendations for oro-dispersible dosage forms (Guidance for the Industry—Orally Disintegrating Tablets—from U.S. Department of Health and Human Services, Food and Drug Administration, Center for Drug Evaluation and Research (CDER) in December 2008), and more preferentially below 20 sec to be able to compete with already existing fast disintegrating hard products (ODT), excluding those manufactured by spray drying/lyophilisation.

Mechanical Properties

The brittleness of the capsules is tested by Tube Test after storage at different relative humidity (RH) conditions. This test is well known to skilled people working in the field of hard capsules and one procedure for its performance is disclosed in the literature (D. Cade and N. Madit, "Liquid Filling in Hard Gelatin Capsules—Preliminary Steps", Bulletin Technique Gattefosse, 1996). During the tests, the % of broken capsule shells in a sample of several tens of shells is evaluated by varying the shell Loss On Drying (LOD): the lower the LOD %, the lower the shell brittleness/mechanical properties, the higher the LOD %, gives the better shell mechanical properties.

EXAMPLES

Example 1

Plantcaps® Hard Capsule from Capsugel with Carbomer Coating

Blue dye is added to the coating for visual purposes to verify the coating application on natural transparent capsules.

Coating 1.1

Aqueous solution comprising 1% Carbopol 974P NF (supplied by Lubrizol company) with 50 ppm Patented Blue (PB) dye.
Spray coating on pullulan-based Plantcaps® hard capsules size 1 with Erweka coating pan equipment at 38° C. during 40 min, according to conventional coating methods known by the person skilled in the art.
About 0.8% weight gain on total capsule weight.

Coating 1.2

Aqueous solution comprising 1% Carbopol 974P NF (supplied by Lubrizol company) with 50 ppm Patented Blue (PB) dye.
Spray coating on pullulan-based Plantcaps® hard capsules size 1 with Erweka coating pan equipment at 38° C. during 3h30, according to conventional coating methods known by the person skilled in the art.
About 1.6% weight gain on total capsule weight.

Comparative Example 1.3

Plantcaps® capsule without coating

Example 2

Plantcaps® Capsule with a Coating Comprising Carbomer and Plasticizer A

Coating 2

Aqueous solution comprising 1% Carbopol 974P NF and 0.2% triacetine (plasticizer A) and 50 ppm PB dye
Spray coating on pullulan-based Plantcaps® capsules size 1 with Erweka coating pan equipment at 37° C. during 45 min, according to conventional coating methods known by the person skilled in the art.

Example 3

Plantcaps® Capsule with a Coating Comprising Carbomer and Plasticizer B

Coating 3

Aqueous solution comprising 1% Carbopol 974P NF and 0.2% Kollisolv P44 (plasticizer B (also known as Lutrol L44 supplied by BASF, or poloxamer 124 HLB 12-18)) and 50 ppm PB dye
Spray coating on pullulan-based Plantcaps® capsules size 1 with Erweka coating pan equipment at 33° C. during 41 min, according to conventional coating methods known by the person skilled in the art.

Example 4

Plantcaps® Capsule with a Coating Comprising Carbomer and Secondary Bio-Adhesive Film Forming Aid Coating 4

Aqueous solution comprising 0.5% Carbopol 974P NF and 0.5% Pullulan polysaccharide having low oligomer content as secondary bio-adhesive film forming aid (supplied by Hayashibara company, Japan) and 50 ppm PB dye
Spray coating on pullulan-based Plantcaps® capsules size 1 with Erweka coating pan equipment at 34° C. during 40 min, according to conventional coating methods known by the person skilled in the art.

Example 5

Plantcaps® Capsule with a Coating Comprising Carbomer and Additional Dissolution Enhancers (C)

Coating 5

Aqueous solution comprising 0.5% Carbopol 974P NF and 5% of a mixture comprising glycerol, polydextrose and maltose as dissolution enhancers C in the relative ratio 2:0.5:1 as described in patent application U.S. Pat. No. 8,105,625 and US 2013/0005831; and 50 ppm PB dye
Spray coating on pullulan-based Plantcaps® capsules size 1 with Erweka coating pan equipment at 35° C. during 42 min, according to conventional coating methods known by the person skilled in the art.

Example 6

Plantcaps® Capsule with a Coating Comprising Carbomer and an Additional Dissolution Enhancer (D)

Coating 6

Aqueous solution comprising 1% Carbopol 974P NF and 0.2% of citric acid as dissolution enhancer D, and 50 ppm PB dye Spray coating on pullulan-based Plantcaps® capsules size 1 with Erweka coating pan equipment at 33° C. during 41 min, according to conventional coating methods known by the person skilled in the art.

Example 7

Plantcaps® Capsule with Coating Comprising Carbomer and an Additional Dissolution Enhancer (E)

Coating 7

Aqueous solution comprising 1% Carbopol 974P NF and 0.2% of guar gum as dissolution enhancer E, and 50 ppm PB dye Spray coating on pullulan-based Plantcaps® capsules size 1 with Erweka coating pan equipment at 35° C. during 40 min, according to conventional coating methods known by the person skilled in the art.

Example 8

Sweetened Plantcaps® Capsule with a Coating Comprising Carbomer, Plasticizer (B) and a Second Muco-Adhesive Polymer

Coating 8

Aqueous solution comprising 0.5% Carbopol 974P NF, 0.5% triacetine, 0.5% Pullulan, and 50 ppm PB dye Spray coating on sweetened pullulan-based Plantcaps® capsules size 1 comprising 5000 ppm (w/w) of *stevia* (Rebaudioside A called Rebaten 97 supplied by Seppic) as described in patent application WO 2013/174884

Spray coating with Erweka coating pan equipment at 35° C. during 40 min, according to conventional coating methods known by the person skilled in the art.

Example 9

Aromatized Plantcaps® Capsule with a Coating Comprising Carbomer, Plasticizer (B) and a Second Muco-Adhesive Polymer

Coating 9

Aqueous solution comprising 0.5% Carbopol 974P NF, 0.5% triacetine, 0.5% Pullulan, and 50 ppm PB dye Spray coating on aromatized pullulan-based Plantcaps® capsules size 1 comprising 5000 ppm of lime aroma (called Limette supplied by Firmenich company) and 0.5% of a salivating mix (proprietary formula supplied by Firmenich company) on total capsule weight.

Spray coating with Erweka coating pan equipment at 35° C. during 40 min, according to conventional coating methods known by the person skilled in the art.

Example 10

Plantcaps® Capsule with a Coating Comprising Alternative Muco-Adhesive (i.e. Bio-Adhesive) Polymer

Coating 10

Aqueous solution comprising 1% sodium carboxymethyl cellulose (Na CMC supplied by Ashland company)

Spray coating on pullulan-based Plantcaps® capsules size 1 with Erweka coating pan equipment at 35° C. during 40 min, according to conventional coating methods known by the person skilled in the art.

Example 11

HPMC-Based Vcaps® Hard Capsule from Capsugel with Carbomer Coating

Coating 11.1

Aqueous solution comprising 1% Carbopol 974P NF (supplied by Lubrizol Company) with 50 ppm Patented Blue (PB) dye.

Spray coating on HPMC-based Vcaps® hard capsule size 1 with Erweka coating pan equipment at 35° C. during 40 min, according to conventional coating methods known by the person skilled in the art.

Comparative Example 11.2

HPMC Vcaps® capsule without coating

Example 12

Gelatin-Based Hard Capsule with Carbomer Coating

Coating 12.1

Aqueous solution comprising 1% Carbopol 974P NF (supplied by Lubrizol Company) with 50 ppm Patented Blue (PB) dye.

Spray coating on gelatin hard capsules size 1 with Erweka coating pan equipment at 35° C. during 40 min, according to conventional coating methods known by the person skilled in the art.

Comparative Example 12.2

Gelatin Hard Capsules without Coating

Observation of Results

Adhesion Results

Figure 1:
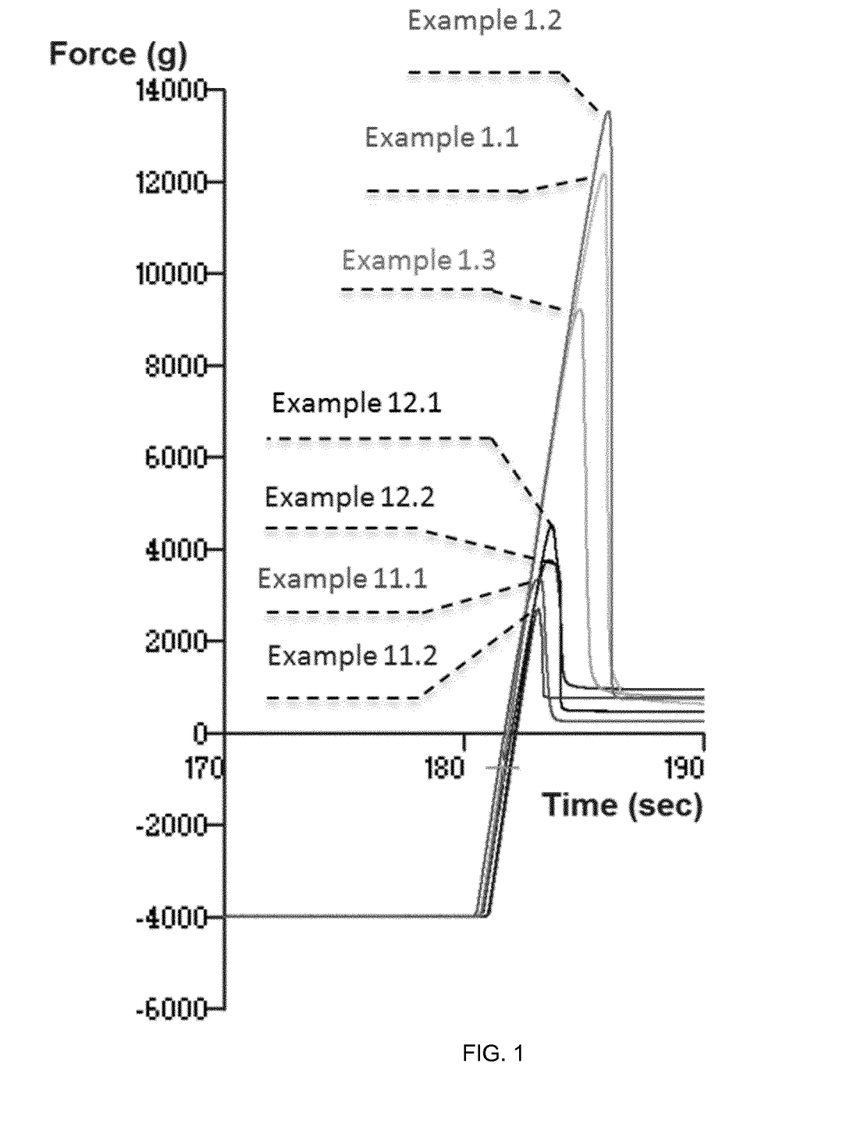
FIG. 1 is a graph showing the adhesion of capsules.

The adhesion forces of coated capsules made of various polymers in contact with aluminum plates are shown in table 1 and FIG. 1.

TABLE 1

| Example # | Max force (g) |
|---|---|
| 1.1 | 12176 |
| 1.2 | 13576 |
| 1.3 | 9707 |
| 11.1 | 3251 |
| 11.2 | 2550 |
| 12.1 | 4522 |
| 12.2 | 3678 |

The presence of Carbomer coating on the hard capsules, whatever their polymer composition—Pullulan, hypromellose or gelatin—shows improvement to the adhesive properties of the dosage forms.

Bio-Adhesion Results

Figure 2:
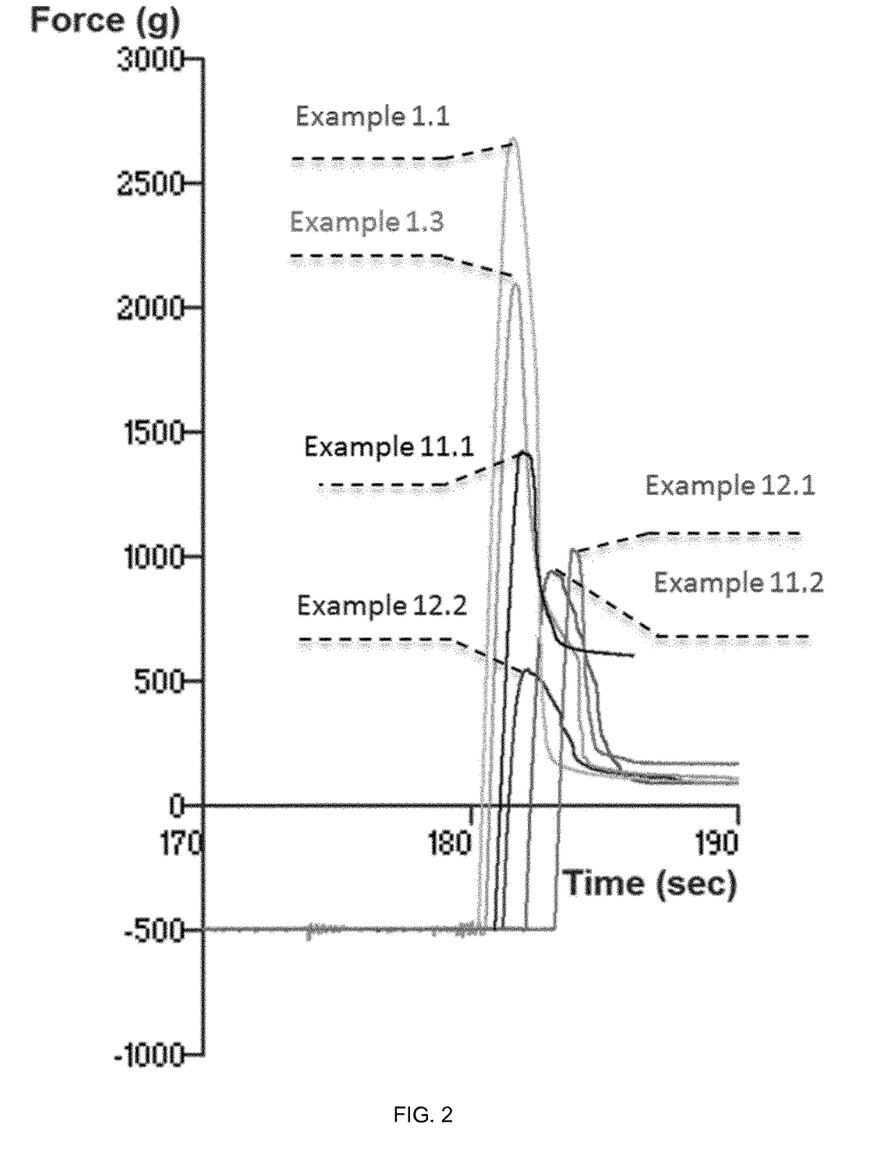
FIG. 2 is a graph showing the bio-adhesion of capsules.

The bio-adhesion forces of coated capsules made of various polymers in contact with pig vaginal mucosa are shown in table 2 and FIG. 2.

TABLE 2

| Example # | Max force (g) |
|---|---|
| 1.1 | 2698 ± 71 |
| 1.2 | 2874 ± 44 |
| 1.3 | 2182 ± 94 |
| 11.1 | 1598 ± 54 |
| 11.2 | 1079 ± 61 |
| 12.1 | 892 ± 72 |
| 12.2 | 629 ± 69 |

The presence of Carbomer coating on the hard capsules, whatever their polymer composition—Pullulan, hypromellose or gelatin, improves the bio-adhesive properties of the dosage forms in contact with a mucosa.

Full Disintegration Test Results

The disintegration times given by the automated endpoint method of coated capsules are given in table 3.

TABLE 3

| Example # | Disintegration time (sec) |
|---|---|
| 1.1 | 63 ± 11 |
| 1.2 | 66 ± 10 |
| 1.3 | 95 ± 9 |
| 2 | 80 ± 13 |
| 3 | 81 ± 11 |
| 4 | 86 ± 8 |
| 5 | 73 ± 6 |
| 8 | 85 ± 9 |
| 9 | 86 ± 9 |
| 11.1 | 155 ± 17 |
| 11.2 | 201 ± 15 |
| 12.1 | 120 ± 18 |
| 12.2 | 130 ± 14 |

The presence of a Carbomer comprising coating particularly on Pullulan-based capsules enables to speed up the complete disintegration of the dosage form by about 30%.

In one embodiment, when the Carbomer is combined with a further muco-adhesive polymer (e.g. pullulan in Ex. 4) in the coating formulation, the coating is visually more satisfying because it presents a smooth surface; the disintegration time benefit is substantially proportional to the Carbomer level in the coating composition.

In one embodiment, the presence of additional dissolution enhancers also enables a gain of disintegration time; nevertheless to a lesser extend compared to pure Carbomer coating.

Vaginal Disintegration Test Results

The disintegration times given by the in vitro method dedicated to suppository and pessary by Eur. Ph. 2.9.2 are given in table 4.

TABLE 4

| | Example # | | |
|---|---|---|---|
| | 1.1 | 1.2 | 1.3 |
| First opening time | 2 min 30 s | 2 min 35 s | 3 min |

The presence of a Carbomer coating on capsules enables to speed up the vaginal disintegration of the dosage form, in particular the first opening time when the filling content starts to be released.

Buccal Disintegration Test Results

The disintegration times given by the in vivo blind test are given in table 5.

TABLE 5

| | Example # | | | |
|---|---|---|---|---|
| | 1.1 | 1.3 | 8 | 9 |
| Capsule opening time | 15 sec | 21 sec | 18 sec | 17 sec |

Although the pullulan-based capsule already shows a good opening time in the mouth of about 20 seconds, it is possible to reduce this time when the capsule are coating with carbomer; it is then possible to reach the 15 sec threshold. This benefit enables to use such capsules for buccal applications, e.g. for people having swallowing difficulties, administration problems, poor compliance issues or when water is not available. The fact that the coated capsules have advanced bio-adhesion properties is also an advantage in the mouth, where capsule can also adhere on the mucosa depending on the salivation rate of the subject.

Mechanical Properties

Tube test results indicate the brittleness tendency of the capsules under stress conditions at reduced humidity. Results are shown in table 6, with the % numbers reporting the % of broken capsules at the respective relative humidity conditions tested.

TABLE 6

| Example # | 45% RH | 33% RH | 23% RH | 10% RH |
|---|---|---|---|---|
| 1.1 | 9% | 22% | 44% | 100% |
| 1.2 | 100% | 100% | 100% | 100% |
| 1.3 | 0% | 0% | 0% | 8% |
| 2 | 4% | 6% | 84% | 100% |
| 3 | 3% | 5% | 51% | 82% |
| 5 | 100% | 100% | 100% | 100% |
| 8 | 1% | 4% | 15% | 80% |
| 9 | 2% | 0% | 14% | 78% |
| 11.1 | 0% | 0% | 0% | 0% |
| 11.2 | 0% | 0% | 0% | 0% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

The invention claimed is:

1. A dosage form article comprising a hard capsule coated with a surface modifying coating composition wherein said coating is an aqueous composition comprising water and one or more muco-adhesive polymers comprising polyacrylates, cellulose derivatives, hyaluronic acid, starch, polyethylene glycol, polysaccharides, collagen derivatives, or mixtures thereof, wherein the ratio of said muco-adhesive polymer to water is less than 0.15, by weight of the coating composition, and wherein said coating is present in an amount of less than 2.5% by weight of the empty capsule.

2. A dosage form article according to claim 1 wherein the ratio of said muco-adhesive polymer to water is from greater than 0.01 to 0.14, by weight of the coating composition.

3. A dosage form article according to claim 1 wherein the coating is present in an amount of less than or equal to 2%, by weight of the empty capsule.

4. A dosage form article according to claim 1 wherein the capsule is made of a shell material comprising gelatin, hydroxypropyl methylcellulose (HPMC), pullulan, or any mixture thereof.

5. A dosage form article according to claim 1 wherein the muco-adhesive polymer comprises a polyacrylate selected from one or more carboxypolymethylenes with an average particle size of less than 0.5 microns.

6. A dosage form article according to claim 5 wherein the carboxypolymethylene comprises a homopolymer of acrylic acid polymerized in ethyl acetate and crosslinked with a polyalkenyl polyether.

7. A dosage form article according to claim 1 wherein the muco-adhesive polymer comprises pullulan.

8. A dosage form article according to claim 1 wherein the coating is applied to the capsule in the form of a liquid.

9. A dosage form article according to claim 1 wherein the muco-adhesive polymer is present in an amount of from 0.5% to 15%, by weight of the coating composition.

10. A dosage form article according to claim 1 wherein at least 80% of the outer surface of said capsule is coated with said coating.

11. A dosage form article according to claim 1 wherein the coating further comprises 0.1% to 5% by weight of said coating composition of one or more plasticizers.

12. A dosage form article according to claim 1 wherein the coating consists of water, the muco-adhesive polymer(s), one or more plasticizers and optionally one or more dissolution enhancers.

13. A method of imparting adhesiveness and rapid capsule disintegration to a hard capsule comprising applying to said capsule an aqueous coating comprising water and one or more muco-adhesive polymers comprising polyacrylates, cellulose derivatives, hyaluronic acid, starch, polyethylene glycol, polysaccharides, collagen derivatives, or any mixture thereof, wherein the ratio of said muco-adhesive polymer to water is less than 0.15, by weight of the coating composition, and wherein said coating is present in an amount of less than 2.5% by weight of the empty capsule.

14. A dosage form article according to claim 1 wherein the coating is a dip coating.

15. A dosage from article according to claim 1 wherein the coating comprises at least two muco-adhesive polymers and wherein at least one of said polymers is a carboxymethylene and at least one other said polymer is pullulan.

16. A dosage form article according to claim 1 wherein the ratio of said muco-adhesive polymer to water is from 0.010 to 0.1.

17. A dosage form article according to claim 1 wherein the ratio of said muco-adhesive polymer to water is from 0.010 to 0.013.

18. A dosage from article according to claim 15 wherein the at one of the at least two muco-adhesive polymers has an average particle size of less than 0.5 microns.

* * * * *

UNITED STATES PATENT AND TRADEMARK OFFICE
CERTIFICATE OF CORRECTION

PATENT NO. : 10,525,011 B2  
APPLICATION NO. : 15/523661  
DATED : January 7, 2020  
INVENTOR(S) : Cade et al.

Page 1 of 1

It is certified that error appears in the above-identified patent and that said Letters Patent is hereby corrected as shown below:

In the Specification

Column 9, Line 58, "remove with" should read --removed with--.

Column 10, Line 14, "mucosa's" should read --mucosas--.

Column 10, Line 26, "remove with" should read --removed with--.

Column 10, Line 39, "automated en-point" should read --automated end-point--.

Column 15, Line 66, "lesser extend" should read --lesser extent--.

Column 16, Line 31, "are coating" should read --are coated--.

In the Claims

Column 18, Line 34, Claim 18, "the at one" should read --the at least one--.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*